(12) United States Patent
Macken (10) Patent No.: US 7,793,661 B2
(45) Date of Patent: Sep. 14, 2010

(54) METHOD AND APPARATUS FOR TREATMENT OF SNORING AND SLEEP APNEA

(76) Inventor: John A. Macken, 233 Twin Pillar Way, Santa Rosa, CA (US) 95404

( * ) Notice: Subject to any disclaimer, the term of this patent is extended or adjusted under 35 U.S.C. 154(b) by 0 days.

(21) Appl. No.: 12/172,132

(22) Filed: Jul. 11, 2008

(65) Prior Publication Data

US 2008/0264427 A1    Oct. 30, 2008

Related U.S. Application Data

(60) Division of application No. 11/102,314, filed on Apr. 8, 2005, now abandoned, which is a continuation-in-part of application No. 10/866,058, filed on Jun. 10, 2004, now abandoned.

(51) Int. Cl.
*A61F 5/37*  (2006.01)
*A61F 5/56*  (2006.01)
*A61F 5/00*  (2006.01)
*A61F 13/00* (2006.01)
*A61F 15/00* (2006.01)

(52) U.S. Cl. .................. 128/848; 128/846; 606/201; 606/204; 604/304; 604/308; 602/41; 602/58

(58) Field of Classification Search .......... 128/845, 128/846, 848, 206.11; 602/18, 41, 58; 606/201, 606/203, 204; 604/304, 308
See application file for complete search history.

(56) References Cited

U.S. PATENT DOCUMENTS

| | | | |
|---|---|---|---|
| 5,176,618 A | | 1/1993 | Freedman |
| 5,476,091 A | * | 12/1995 | Johnson ................. 128/200.24 |
| 5,643,315 A | * | 7/1997 | Daneshvar ................. 606/201 |
| 6,098,616 A | * | 8/2000 | Lundy et al. ........... 128/200.24 |
| 6,357,436 B1 | * | 3/2002 | Kreitzer et al. ......... 128/200.24 |
| 6,375,667 B1 | * | 4/2002 | Ruch ......................... 606/199 |
| 6,390,089 B1 | * | 5/2002 | Lacouture ............. 128/200.24 |
| 6,470,883 B1 | * | 10/2002 | Beaudry ................ 128/200.24 |
| 6,631,714 B2 | * | 10/2003 | Von Duyke et al. .... 128/200.24 |
| 6,955,172 B2 | | 10/2005 | Nelson et al. |
| 7,188,627 B2 | | 3/2007 | Nelson et al. |
| 2001/0032645 A1 | * | 10/2001 | Cronk et al. ........... 128/200.24 |
| 2003/0056785 A1 | | 3/2003 | Narihiko et al. |
| 2004/0112390 A1 | | 6/2004 | Brooks et al. |
| 2005/0066965 A1 | * | 3/2005 | Cronk et al. ........... 128/200.24 |

* cited by examiner

*Primary Examiner*—Patricia M Bianco
*Assistant Examiner*—Brandon Jackson
(74) *Attorney, Agent, or Firm*—Craig M. Stainbrook; Stainbrook & Stainbrook, LLP (57) ABSTRACT

An anti-snoring device that attaches to a specific area of the neck. The attachment means can be an adhesive, a clip or an implant. The device exerts a predetermined pulling force on this area of the neck, causing this area of the neck to expand outward from its normal position. This expansion opens a blockage in the throat of a sleeping person, thereby eliminating snoring and helping some people with obstructive sleep apnea.

7 Claims, 7 Drawing Sheets

METHOD AND APPARATUS FOR TREATMENT OF SNORING AND SLEEP APNEA

CROSS REFERENCE TO RELATED APPLICATIONS

The present application claims the benefit of the filing date of U.S. patent application Ser. No. 11/102,314, filed Apr. 8, 2005, which claims the benefit of U.S. patent application Ser. No. 10/866,058, filed Jun. 10, 2004, now abandoned.

STATEMENT REGARDING FEDERALLY SPONSORED RESEARCH OR DEVELOPMENT

Not applicable.

REFERENCE TO A MICROFICHE APPENDIX

Not applicable.

TECHNICAL FIELD

The present invention relates generally to health and medical devices, and more particularly to an improved method and apparatus for the treatment of snoring and sleep apnea.

BACKGROUND INFORMATION AND DISCUSSION OF RELATED ART

The fundamental cause of snoring is a restriction or blockage of the air passage in the throat. This occurs when muscles relax during sleep allowing soft tissue in the back of the throat to sag. This soft tissue then blocks the flow of air needed for breathing. Most people that snore overcome this blockage by breathing harder, and the increased air pressure partially opens up the air passage. The snoring sound is the restricted airflow vibrating the soft tissue. Besides the obvious noise, the snoring person also has laborious breathing that decreases the quality of sleep. In extreme cases of air passage blockage, there is a medical condition called obstructive sleep apnea where the quality of sleep is severely degraded.

There are hundreds of patents relating to anti-snoring devices. Almost all the mechanical devices that have been developed simply do not treat the fundamental cause of snoring because they do not open up the blocked air passage in the throat. There are two classes of mechanical anti-snoring devices that actually open up this blocked air passage. The first class opens the blocked air passage in the throat by forcing the lower jaw to jut forward to an unnatural position. However, these devices that force the lower jaw forward are very uncomfortable and can cause alignment problems with the teeth.

The second class of anti-snoring devices that opens the blocked air passage in the throat utilizes an air mask, a hose and a low-pressure air compressor to inflate the lungs and air passages to a pressure typically between 70 and 120 Pascal above atmospheric pressure (a pressure between about 7 mm and 12 mm of water). This class of device is usually called a CPAP machine (Continuous Positive Airways Pressure machine). These machines are expensive, uncomfortable and restrictive. About half of the people that start using CPAP machines to treat sleep apnea cannot tolerate them and discontinue their use.

All the known prior art anti-snoring devices that utilize an adhesive are intended to be worn somewhere on the face. These devices open the nose, distort the cheek or cover the mouth. None of these prior art adhesive devices stop snoring by expanding a portion of the neck to open up the blocked air passage in the throat.

For example, the following patents utilize an adhesive device to cover the mouth: French Patent No. 78 08083 to Blander; German Patent No. DE 3837277 to Obermeler; and U.S. Pat. No. 4,817,636 to Woods.

The following patents utilize an adhesive or suction device on the nose: U.S. Pat. No. 1,292,083 to Sawyer; U.S. Pat. No. 6,631,714 to Von Duyke; U.S. Pat. No. Re. 35,408 to Petruson; and U.S. Pat. No. 3,594,813 to Sanderson.

The following patents utilize an adhesive device on the cheek: U.S. Pat. No. 3,782,372 to Carlton; and U.S. Pat. No. 5,752,524 to Corcoran.

All the known prior art anti-snoring devices that utilize an implant utilize an implant in the soft palate to alter the dynamic response and reduce snoring. No prior art anti-snoring patents use an implant to expand an external part of the neck. Typical soft palate implant patents are: U.S. Pat. Nos. 6,848,447 6,634,362 6,601,585 6,578,580 6,523,543 to Conrad and U.S. Pat. Nos. 6,626,181 6,601,584 6,523,542 to Knudson.

U.S. Pat. No. 5,592,938 to Scarberry describes a body part enclosure comprising a sheath or rap that can be made rigid by the application of a vacuum. One of the applications briefly mentioned for this device is a sheath to create a partial vacuum on the neck as a treatment for sleep apnea. The vacuum is intended to draw out tissue and expand the airway during sleep to relieve airway obstruction. No specific design is given for a device that would treat sleep apnea.

The Scarberry prior art requires that the vacuum device be attached to a vacuum pump to compensate for minor leaks. Also, movement of a sleeping person can break the vacuum seal and cause a major leak. There will also be a strong pushing force exerted on the seals and this will tend to nullify any possible beneficial effect obtained from the vacuum expansion of other tissue. The invention herein is much more practical. The invention avoids the problems associated with vacuum by using mechanical means to connect to the skin.

The foregoing patents reflect the current state of the art of which the present inventor is aware. Reference to, and discussion of, these patents is intended to aid in discharging Applicant's acknowledged duty of candor in disclosing information that may be relevant to the examination of claims to the present invention. However, it is respectfully submitted that none of the above-indicated patents disclose, teach, suggest, show, or otherwise render obvious, either singly or when considered in combination, the invention described and claimed herein.

BRIEF SUMMARY OF THE INVENTION

The method and apparatus for treatment of snoring and sleep apnea of this invention provides a mechanical means to exert a predetermined force on a predetermined area of the neck, causing this area of the neck to expand outward from its normal position. This expansion opens a blockage in the throat of a sleeping person, thereby eliminating snoring and helping some people with obstructive sleep apnea. The mechanical means includes adhesive patches, mechanical clips and magnetic implants which receive a pulling force from an external means.

The present invention describes how humans have multiple responsive points within a specific area of the neck (hereafter called the "throat stimulation area") that exhibit the ability to stimulate the throat in such a way as to open the blockage in the air passage of a sleeping person. This eliminates snoring and sleep apnea in some people. To achieve this result, the surface of the skin in at least a portion of the throat stimulation area must be pulled so that the surface of the skin is extended by at least 2.5 mm beyond the normal position. The invention provides an attachment device, such as an adhesive coated patch, that attaches to the skin within the throat stimulation area and preferably over a responsive point. Pulling on this patch (or other attachment device) expands the skin and maintains an open-air passage in a sleeping person. The snoring sound is reduced or eliminated and even some people with obstructive sleep apnea can have their breathing passage opened by this invention.

In the preferred embodiment, adhesive patches are attached to the skin to cover two responsive points along the left and right edges of the trachea. The pulling force to expand these areas is generated by a separate springy connector that pulls both patches apart with a predetermined force. Other adhesive based embodiments are also disclosed such as an elastic bridge and a cantilevered patch. Additional embodiments include clips that physically grab and pull a portion of the skin and magnetic implants which can be externally pulled to expand the surface of the skin.

It is therefore an object of the present invention to provide a new and improved method and apparatus for treatment of snoring and sleep apnea.

It is another object of the present invention to provide a new and improved anti-snoring device.

A further object or feature of the present invention is a new and improved anti-snoring device, which is comfortable in use.

An even further object of the present invention is to provide a novel anti-snoring device that expands a portion of the user's neck to facilitate breathing.

Other novel features which are characteristic of the invention, as to organization and method of operation, together with further objects and advantages thereof will be better understood from the following description considered in connection with the accompanying drawing, in which preferred embodiments of the invention are illustrated by way of example. It is to be expressly understood, however, that the drawing is for illustration and description only and is not intended as a definition of the limits of the invention. The various features of novelty, which characterize the invention, are pointed out with particularity in the claims annexed to and forming part of this disclosure. The invention resides not in any one of these features taken alone, but rather in the particular combination of all of its structures for the functions specified.

There has thus been broadly outlined the more important features of the invention in order that the detailed description thereof that follows may be better understood, and in order that the present contribution to the art may be better appreciated. There are, of course, additional features of the invention that will be described hereinafter and which will form additional subject matter of the claims appended hereto. Those skilled in the art will appreciate that the conception upon which this disclosure is based readily may be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the Abstract is to give a brief and non-technical description of the invention. The Abstract is neither intended to define the invention of this application, which is measured by the claims, nor is it intended to be limiting as to the scope of the invention in any way.

Certain terminology and derivations thereof may be used in the following description for convenience in reference only, and will not be limiting. For example, words such as "upward," "downward," would refer to directions in the drawings to which reference is made unless otherwise stated. The following description has numerous examples relating to the human body. For simplicity, examples will often only refer to areas on the left side of the neck. All examples that refer only to the left side of the neck apply equally to the right side of the neck. References in the singular tense include the plural, and vice versa, unless otherwise noted.

BRIEF DESCRIPTION OF THE SEVERAL VIEWS OF THE DRAWINGS

The invention will be better understood and objects other than those set forth above will become apparent when consideration is given to the following detailed description thereof. Such description makes reference to the annexed drawings wherein.

DETAILED DESCRIPTION OF THE INVENTION

The instant application is a continuation-in-part of U.S. Utility patent application Ser. No. 10/866,058, filed Jun. 10, 2004, which application is incorporated in its entirety by reference herein.

Referring now to FIGS. 1 through 15, wherein like reference numerals refer to like components in the various views, there is illustrated therein a new and improved anti-snoring device.

Figure 1:
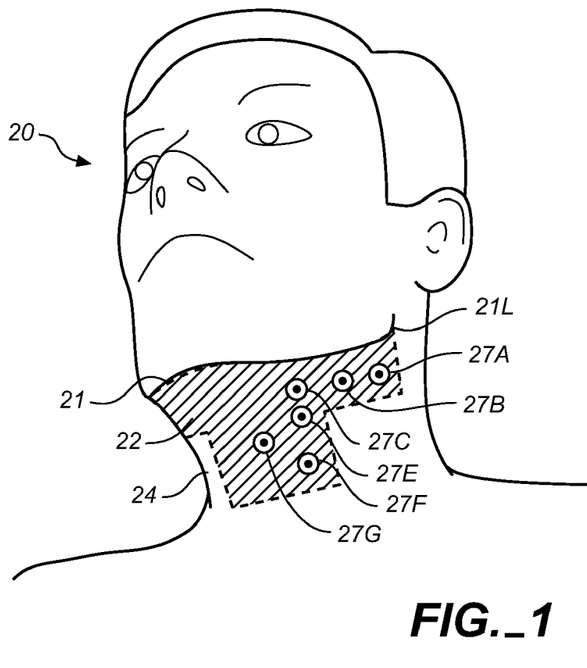
FIG. 1 is a perspective view of a human to illustrate the portion of the neck containing the throat stimulation area and responsive points.

FIG. 1 shows a human 20 with a neck 24. The lower edge of the jawbone is 21 (hereafter called the "jawbone line"). The left end of the jawbone is 21L. There is a "T" shaped area 22 below the jawbone 21 that will be called the "throat stimulation area". Within the throat stimulation area there are several points collectively designated as 27 that will be called "responsive points". FIG. 1 illustrates responsive points 27 A, B, C, E and F that are on the left side of the neck. Each of these points has a comparable point on the right side of the neck, but points on the right side are not illustrated here for simplicity. Point 27G is in the center of the neck, so there are a total of 11 responsive points (including 5 points on the right not illustrated). Responsive points 27A, 27B and 27C all are located about 1.5 cm below the jawbone line 21. Responsive point 27E is located along the left edge of the trachea (windpipe) and about 3 cm below the jawbone line 21. Point 27E is most easily located because it is very near the portion of the neck where the carotid artery produces a strong pulse. Point 27F is also along the left edge of the trachea and about 3 cm below point 27E. Point 27G is located on the center of the trachea. Not all the responsive points work the same way and these differences will be discussed later. Points 27E (left and right side) are believed to be the most important of the 11 responsive points.

Throat stimulation area 22 in FIG. 1 encompasses all the responsive points. This throat stimulation area is "T" shaped and the top of the "T" extends from the left end of the jawbone 22L to the right end of the jawbone (not shown). This top portion of the "T" extends about 3 cm below the jawbone line 21. The vertical portion of the "T" includes the trachea and extends about 1.5 cm beyond the left and right edge of the trachea.

An experiment was performed using a flat piece of plastic that was 21 square centimeters in area. The plastic was adhered to a subject's neck using double coated tape and covered responsive points 27A, B, C and E. The subject then relaxed muscles in his jaw and neck. This caused the subject's breathing passage to close because the subject suffers from sleep apnea and relaxing the neck muscles simulated the sleeping condition. Very laborious breathing could partly open the breathing passage and caused a snoring sound. It was found that pulling on the plastic immediately opened the blocked air passage. In fact, it was nearly impossible to make a snoring sound as long as there was a pulling force on the plastic and as long as the jaw was positioned with the lower teeth slightly separated from the upper teeth.

The amount of force required to stop the simulated snoring depended on whether the head was tilted forward or back and also depended on the degree of opening between the lower and upper jaw. The simulated snoring sound stopped for a specific head position when the pulling force reached 0.25 Newton (about 25 gram force). This is equivalent to lowering the external pressure on the area covered by the patch by about 120 Pascal (about 12 mm of water). This 120 Pascal pressure reduction is the exact opposite of the 120 Pascal pressure increase sometimes used by CPAP machines to open a blocked air passage. This pressure similarity might not be a coincidence since the internal pressure exerted by CPAP machines also expands the portion of the neck covered by the patch. It is possible that some of the benefit of CPAP machines is the result of expanding this area. In any case, it appears that in some people, lowering the pressure on just the outside surface of the neck has a similar beneficial effect to raising the internal pressure on the entire respiratory system.

Not all snoring and sleep apnea sufferers have the same cause of throat blockage. For example, the shape of tonsils, the tong and the soft pallet differ. There may be additional responsive points within the throat stimulation area that can be found experimentally by those of ordinary skill in the art. Therefore, the teaching here is that there are multiple responsive points within the throat stimulation area that can reduce snoring when the skin over one or more responsive point is pulled to expand (lift) the surface by at least 2.5 mm beyond the normal position.

Figure 2:
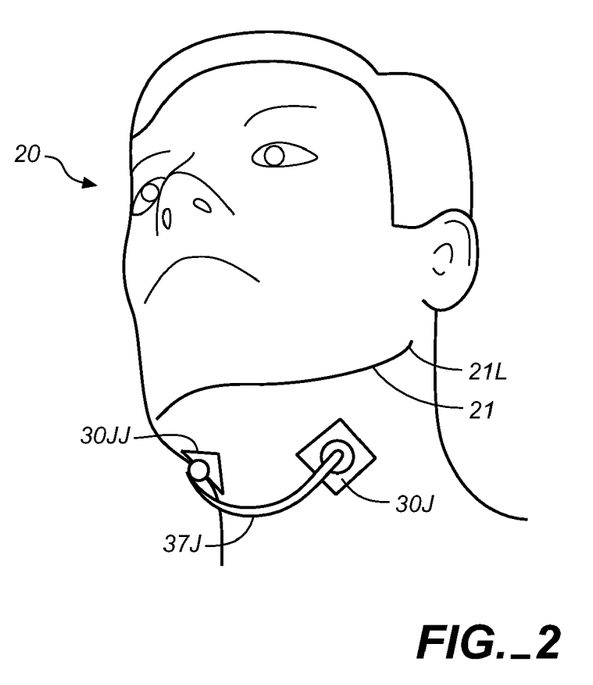
FIG. 2 is a perspective view of a human wearing the preferred embodiment of anti-snoring device; a dual adhesive patch with a bow type elastic connector.

FIGS. 2 through 5, taken together, show the preferred embodiment of this invention. FIG. 2 shows a human, 20, with two adhesive anti-snoring patches, 30J and 30JJ. These two patches are attached together by an elastic connector, 37J that will be called either a "bow connector" or an "elastic connector in compression". The bow connector attempts to separate 30J and 30JJ and provides the required pulling force on each patch. The patches 30J and 30JJ are illustrated as being placed over previously described responsive points 27E (left and right). When this placement is used, successful results have been obtained when the bow connector has a pulling force of 0.36 Newton (37 gram force).

Figure 3:
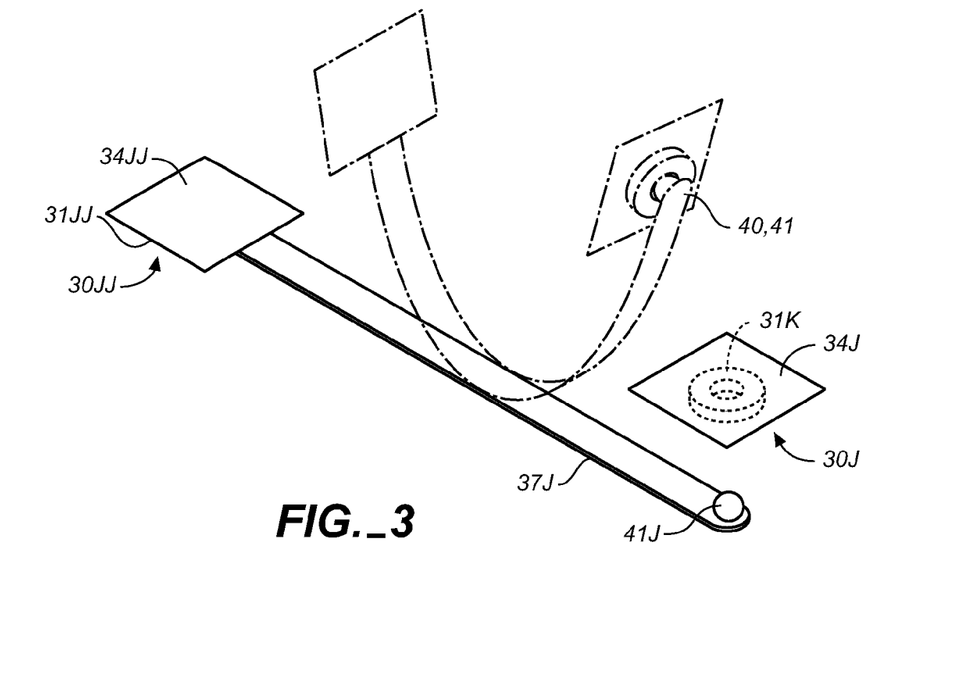
FIG. 3 is a perspective view of the bow type elastic connector depicted in FIG. 2.

FIG. 3 illustrates the flexibility of the bow connector, 37J. The solid line drawing shows bow connector 37J when no force is being exerted. However, bow connector 37J is a springy material and can elastically bent (compressed) into the position shown by the dashed line drawing in FIG. 3. Successful tests have used strips of either 0.75 mm or 0.62 mm thick polycarbonate plastic for bow connector, 37J.

Figure 4:
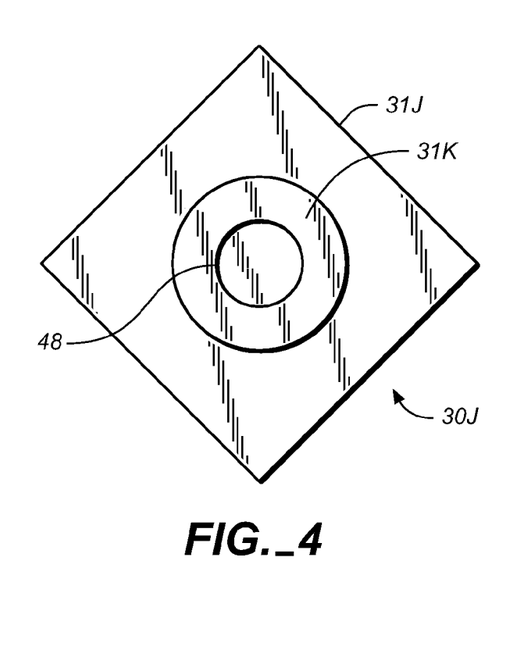
FIG. 4 is a plan view of one of the adhesive patches depicted in FIGS. 2 and 3.
Figure 5:
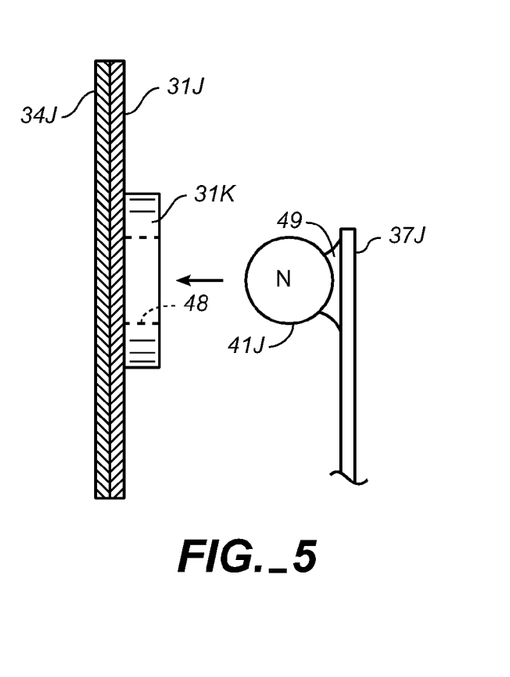
FIG. 5 is a side view in elevation of the adhesive patch depicted in FIG. 4 showing its coupling relationship to the elastic connector device depicted in FIG. 3.

FIGS. 3, 4, and 5 illustrate the preferred method of attaching (coupling) the bow connector 37J with patches 30J and 30 JJ. It is desirable that the patches can be oriented at different angles to accommodate different size people. This calls for a coupling means that has the characteristic of a ball joint. Another desirable characteristic is the ability to easily attach and remove the patches from the flexible bow connector.

The solution is another invention by this inventor and described in a patent application titled "Method and Apparatus for Magnetic Coupling". Briefly, FIG. 5 shows a spherical magnet 41J attached to bow connector 37J by glue 49. The letter "N" represents the north pole of the magnet. This implies that the magnetic axis is pointing out of the page. This magnetic orientation means that the spherical magnet 41J will be drawn towards a hole 48 in the steel disk 31K. The diameter of hole 48 is optimally slightly smaller than the diameter of the spherical magnet. When spherical magnet 41J contacts the hole 48, it forms a magnetic coupling with the ball joint and release properties previously described.

While this is the preferred coupling means, it is not necessary to use this coupling means to attach patches 30J and 30JJ to the bow coupler 37J. In fact, any elastic means in compression, such as a spring, can be used to supply the required force to separate patches 30J and 30JJ.

In one test, the size of bow connector, 37F, was adjusted so that it exerted a 0.33 Newton pulling force (about 34 gram force) on patches 31J and 31JJ. This force was sufficient to open the blocked air passage for a person who suffers from obstructive sleep apnea. Less force may be required for a person with just a snoring problem.

FIGS. 4 and 5, taken together, show details of the construction of patches 30J and 30JJ. The thicknesses of components in FIG. 5 are exaggerated for clarity. In the preferred embodiment, 31J and 34J together are a piece of tape. 34J is the adhesive side of the tape and 31J is the carrier or support member for the adhesive. Similarly, 31JJ and 34JJ are another piece of tape. 31K is another type of support member for the adhesive 34J. In the preferred embodiment, 31K is a steel disk with a hole 48. The steel disk 31K provides the desired stiffness and area so that the experimentally determined optimum area is skin is expanded by the pulling action of the connector.

The adhesive could have been applied directly to disk 31K, but it has been experimentally determined that the best adhesion and comfort occurs when the support for the adhesive has both a stiff component 31K and a flexible component (the portion of 31J that extends beyond the edge of 31K).

Figure 9:
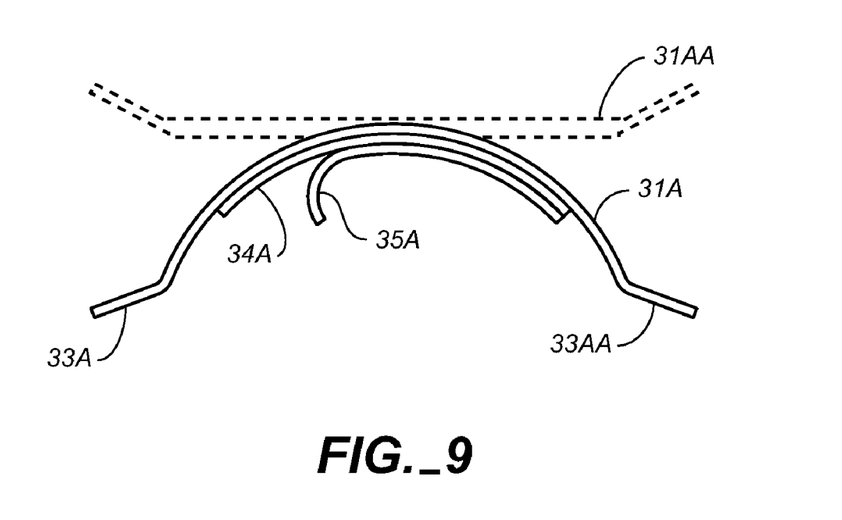
FIG. 9 is a side elevation view of the bridge type anti-snoring device depicted in FIGS. 6, 7 and 8.

Other shapes and materials (such as plastic or rubber) can be used for the support member 31 of the adhesive. The reason for the use of steel in the preferred embodiment is to make easy attachment and removal using magnets. Also the use of tape simplifies construction, but it is desirable to cover the adhesive 34J with a release liner prior to usage. A release liner that can be peeled off is illustrated in FIG. 9 and this means of protecting the adhesive is desirable with any adhesive anti-snoring device. Therefore, FIG. 5 illustrates the device after the release liner has been removed.

In experiments, 31J and 34J together were a piece of tape, 25 mm×25 mm×0.8 mm thick. Ferromagnetic material 31K was a 0.75 mm thick steel washer, 16 mm outer diameter and 5.6 mm inner diameter. This steel washer was attached to tape 31J. The spherical magnet 41J was 6.35 mm (¼ inch) in diameter and made from the rare earth magnetic material known as NdFeB. The patches 30J and 30JJ were attached to the test subject as shown in FIG. 1. The diamond orientation of the square patches was used because this minimized skin irritation. The patches were applied over points 27E previously described in FIG. 1. The bow coupler 37J was then attached using the magnets previously described.

If the test subject normally sleeps with his jaw completely closed (teeth contacting), and if the blockage is strong, then it is advisable for the subject to also wear a commercially available dental spacer to slightly separate the teeth. This is a plastic device that fits over the front two teeth and is usually used to prevent grinding of the teeth. This device is completely different from oral anti-snoring devices that cause the jaw to jut forward unnaturally. Those oral anti-snoring devices are uncomfortable, and can shift the position of teeth.

Figure 6:
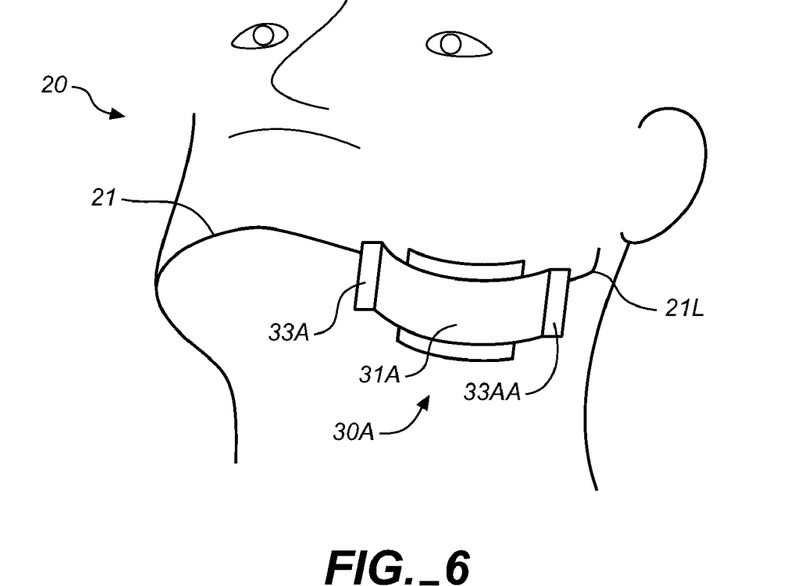
FIG. 6 is a perspective view of a bridge type anti-snoring device attached parallel to the jawbone.
Figure 7:
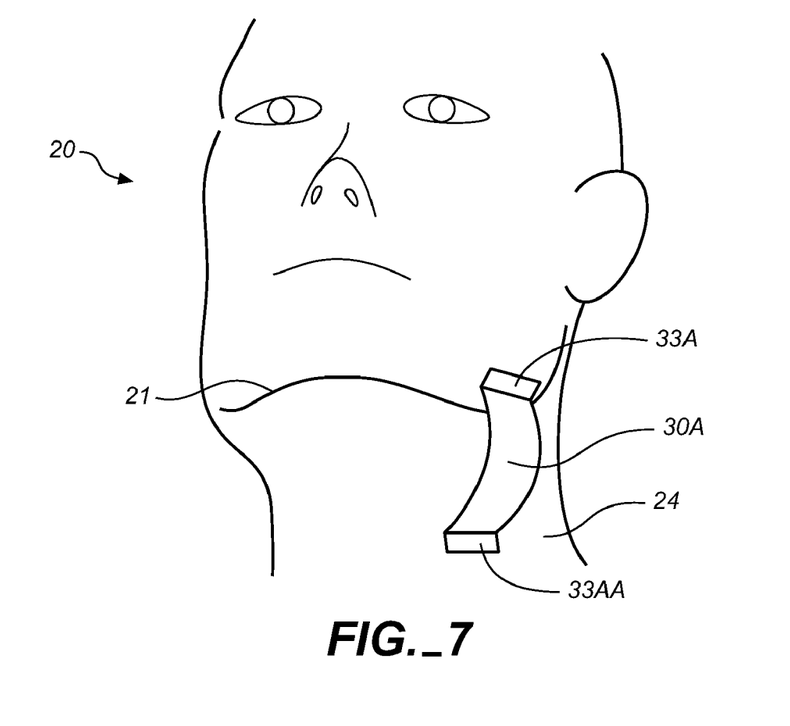
FIG. 7 is a perspective view of a bridge type anti-snoring device attached perpendicular to the jawbone.

FIGS. 6 and 7 show a bridge type neck patch type anti-snoring device, 30A, attached to a human, 20. This device is used to expand one or more of responsive points 27A, B, C or E described in FIG. 1. In FIG. 6 the orientation of 30A is generally parallel to the jaw line 21 and in FIG. 7 the orientation is generally perpendicular to 21. As will be described in FIGS. 8 and 9, device 30A consists of a support member 31A and an adhesive layer. The adhesive, not visible in FIG. 6 or 7, is attached to the skin covering at least a portion of the previously designated throat stimulation area. Pads 33A and 33AA push on the skin in the vicinity of the jawbone line 21 in FIG. 6. In FIG. 7 pad 33A pushes on the jawbone 21 and pad 33AA pushes on a portion of the neck 24.

Figure 8:
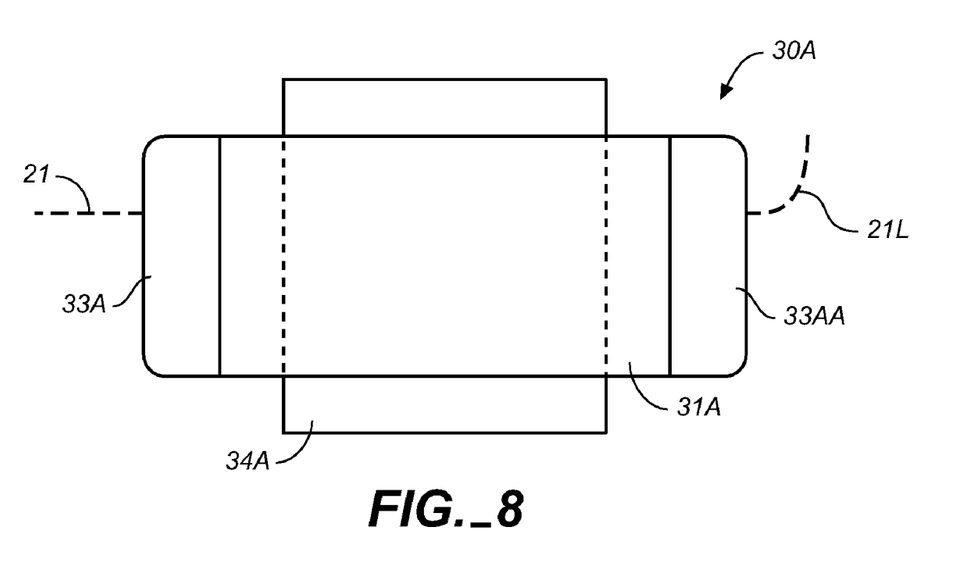
FIG. 8 is a top plan view of the bridge type anti-snoring device depicted in FIGS. 6 and 7.

FIGS. 8 and 9, taken together, show the bridge type anti-snoring device, 30A, of FIGS. 6 and 7. Support member, 31A, has an adhesive coating, 34A, on it's inside surface. This adhesive can be either double coated tape or an adhesive coating directly on member, 31A. FIG. 9 shows an embodiment where adhesive, 34A, is double coated tape. This double-coated tape preferably extends beyond two edges of the support member, 31A as seen in FIG. 8. FIG. 9 also shows a release liner, 35A, on the surface of adhesive, 34A. Normally, this release liner would be present before the neck patch anti-snoring device is used. Just prior to application, the user would peel off liner, 35A, exposing the adhesive surface, 34A. The remainder of the discussion of FIG. 9 will presume that the release liner, 35A, has been removed.

It is most desirable for support member, 31A, to be flexible. FIG. 9 shows this flexibility. Support member, 31A, would have the shape shown by the solid line drawing in FIG. 9, when there is no force bending this support member. However, pushing on 31A can cause it to flatten as shown by the dashed line, 31AA, in FIG. 9. Once adhered to the skin, the member, 31A in FIG. 9, attempts to spring back to the solid line drawing in FIG. 9. However, since the adhesive, 34A, is now attached to the skin, the flexible support member 31A can only partly spring back to the starting shape of member 31A in FIG. 9. This exerts a predetermined pulling force on the skin that is being adhered to the adhesive, 34A. This pulling force expands the throat stimulation area and causes the skin of the throat stimulation area to protrude beyond its normal position by at least 2.5 mm.

When the anti-snoring device shown in FIG. 9 is being worn, the predetermined pulling force exerted by the flexible support member reduces the height of the arch to considerably less than the arch shown in FIG. 9. This intentional flexing also straightens out the pressure surfaces, 33A and 33AA, in FIG. 9 so that they press approximately flat on the skin over the jawbone.

It is not essential that the support member be flexible since the skin is flexible and it is possible to apply even a rigid neck patch anti-snoring device by deforming the skin sufficiently during application. However, it is most desirable to use a springy material such as springy plastic, metal, rubber or urethane for support member, 31A.

One successful device had the shape shown in FIGS. 8 and 9. This device had support member 31A made of 0.5 mm thick polycarbonate plastic, with dimensions of 7 cm×2.8 cm and an unloaded arch height of about 2 cm. The tape, 34A, extended about 6 mm beyond the top and bottom edge of the plastic. The optimum arch height varies with individuals and depends on factors such as the tightness of the skin and the degree of air passage blockage.

In FIG. 9, the ends of support member, 31A, are shown as being somewhat flattened and the flattened surfaces are designated 33A and 33AA. These will be designated as "pressure surfaces". Most of the pushing force counteracting the pulling action of the adhesive is transmitted through these pressure surfaces. It is not necessary for them to be flattened, but this is desirable to distribute the pushing force and prevent irritation of the skin.

In FIGS. 8 and 9, the adhesive area, 34A, is shown extending beyond the edges of support member, 31A, but not extending over the entire width of the support member, 31A. This partial width coverage is easier to illustrate and seems to work well. The adhesive, 34A, is depicted as being double coated adhesive tape since it extends beyond the edge of member, 31A. This adhesive extension is desirable, but not necessary. Extending the tape, beyond the edge of member, 31A, helps the adhesion of the tape to the skin.

FIG. 8 also shows the preferred placement of the anti-snoring device, 30A, relative to the jawbone line, 21, and the left end of the jawbone, 21L. It can be seen that dashed line, 21, (representing the lower edge of the jawbone) is not centered on device, 30A. Also, pressure surface, 33AA, is near the left end of the jawbone, 21L. This positioning centers part of the arch over one or more of the throat stimulation areas 27 in the throat stimulation area 22 in FIG. 1.

Figure 10:
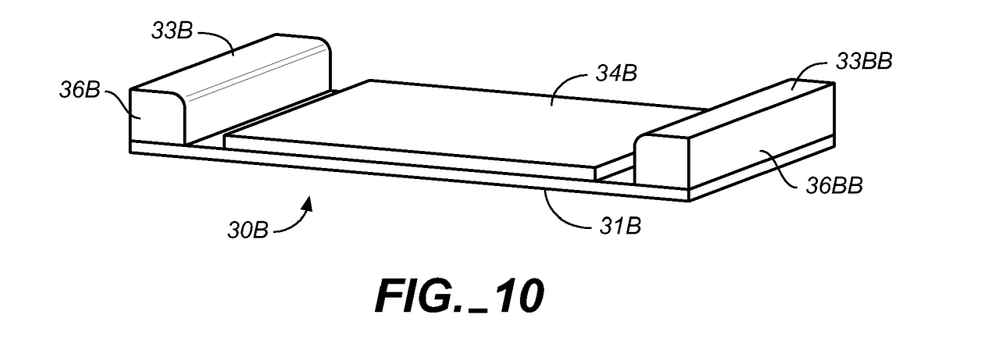
FIG. 10 is a perspective view of a bridge type anti-snoring device constructed with soft support pads.

FIG. 10 shows another bridge type anti-snoring device, 30B, which is similar to device 30A illustrated in FIGS. 8 and 9. In this variation, the support member is designated 31B, the adhesive surface is 34B and the pressure surfaces are 33B and 33BB. The adhesive, 34B, is illustrated thicker than normal for clarity. In this example, support member, 31B, is shown as a generally flat material, but curved shapes are also possible. Member, 31B, can be either flexible or rigid. The key point in this embodiment is that soft pads, 36B and 36BB, have been added to member, 31B. These pads can be made of any suitable material, but the preferred material is foam rubber or foam urethane. The outer surfaces of these pads form the pressure surfaces, 33B and 33BB. These pads can also be removable or applied after the adhesive is attached to the skin.

The design depicted in FIG. 10 is shown with a similar projected shape to the design in FIG. 8. The design in FIG. 10 could also be positioned as shown in FIG. 6 or 7. However, it should be understood that the size and position of both the soft pads and the support member can be modified in any way to accomplish the goal of expanding the throat stimulation area beyond its normal position. In general, soft pads can be substituted for contours in the shape of the support member, 31, in any figure.

The term "bridge type" anti-snoring device is used to describe the devices in FIGS. 6 through 9. This is because the characteristic of a bridge type anti-snoring device is to have a central region positioned above a portion of the throat stimulation area, and between two or more supports. The device depicted in FIG. 6, through 9 has an arch shape, while the device depicted in FIG. 10 is planar. However, both devices have the characteristics of a bridge. Other bridging shapes are also possible.

Figure 11:
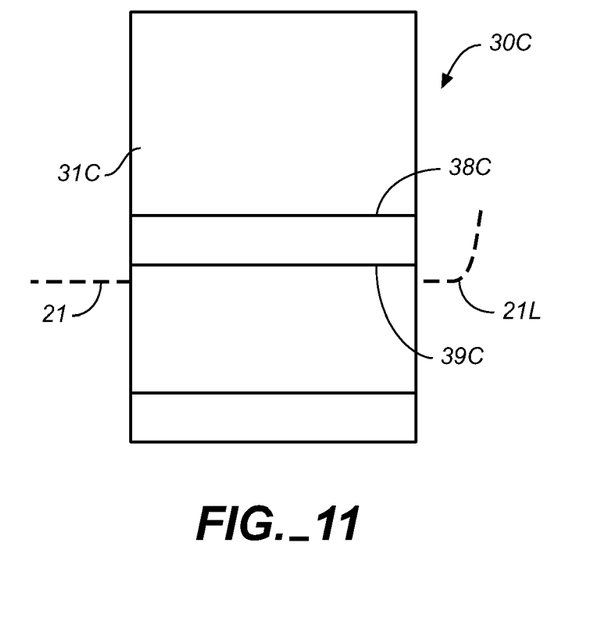
FIG. 11 is a top plan view of a cantilever type embodiment of an anti-snoring device of this invention.
Figure 12:
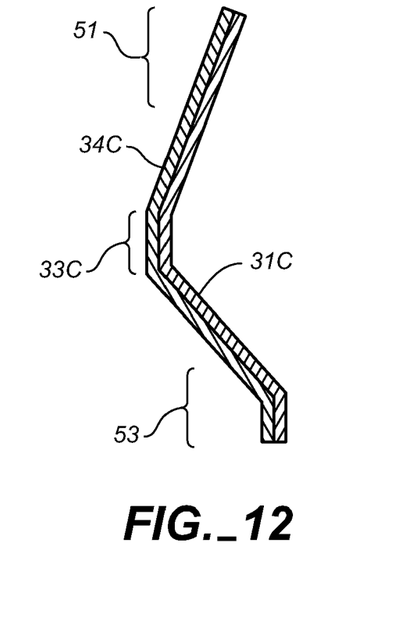
FIG. 12 is a side elevation view of the cantilever type anti-snoring device depicted in FIG. 11.

FIGS. 11 and 12, taken together, illustrate a cantilever type anti-snoring device, 30C. A cantilever type anti-snoring device applies a pulling force on the desired region of the throat stimulation area by pushing on the jawbone and pulling on the cheek. In FIGS. 11 and 12, there is a support member 31C, and an adhesive 34C. This device is illustrated as being bent with fold lines, 38C and 39C. Experiments have had the structural material made out of 0.5 mm or 0.75 mm thick polycarbonate plastic. When applied to a person, this flexible material straightens out somewhat compared to the amount of bend illustrated in FIG. 12.

When the device in FIGS. 11 and 12 is applied to a person, it is positioned similar to FIG. 7, except that device 30C is positioned higher. FIG. 11 shows the proper positioning of the anti-snoring device, 30C, relative to jawbone line, 21. The left end of the jawbone is 21L. It can be seen that the proper placement of this device has the fold line, 38C, slightly above the jawbone line, 21, so that pressure surface, 33C, presses against the jawbone through the skin. The lower half of the anti-snoring device, 30C, is cantilevered out past the jawbone line, 21, and pulls on the skin of the throat stimulation area, preferably over one or more responsive points. In particular, region 53 in FIG. 12, applies the pulling force to the desired part of the throat stimulation area. The cheek exerts a counterbalancing pulling force because region 51 is adhered to the cheek and the jawbone acts like a fulcrum.

Some individuals with only a slight snoring problem and tight skin may be able to have no fold lines so that support member 31C is flat. Even a flat support member will exert some pulling force on throat stimulation area, 22L. This is because a normal weight person has the skin of the throat stimulation area indented below the jawbone line, 21. Pulling this skin out with a flat surface is actually expanding the throat stimulation area by at least 2.5 mm.

Figure 13:
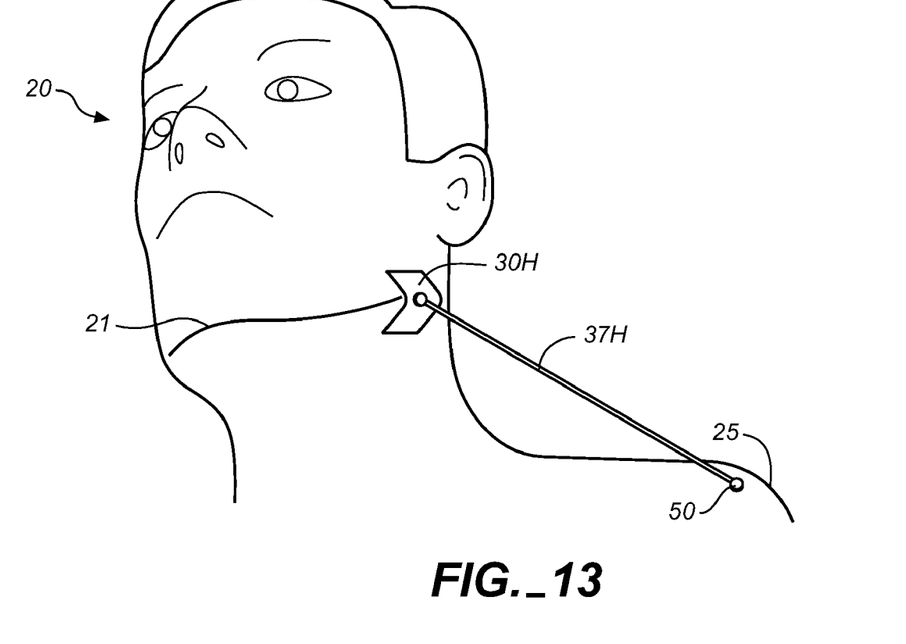
FIG. 13 is a perspective view of an elastic connector in a tension pulling on an adhesive patch anti-snoring device.

FIG. 13 shows an "elastic connector in tension" type anti-snoring device. Adhesive patch, 30H, is a piece of adhesive tape with a connection means such as a 6 mm diameter magnet captured between the tape and the skin. Elastic connector, 37H, in FIG. 13 is connected to an anchor point, 50, located on the shoulder, 25. The elastic connector, 37H, has been stretched so that it is in tension and exerts a pulling force on at least one throat stimulation area in the throat stimulation area (not illustrated, but located under 30H). The elastic connector in tension, 37H, could be any material or device that can maintain a predetermined pulling force such as a rubber band or a spring. It would also be possible to use a device such as a spring loaded rewind spool similar to a rewind tape measure device.

The anchor point, 50, is shown on the shoulder, but this anchor point could be on other parts of the body such as the chest, back, or waist. The exact method of attaching to the anchor point is not important. For example, the anchor point is illustrated in FIG. 13 as if it were a real point. In practice, it could be any attachment means such as a loop under the arm.

Figure 14:
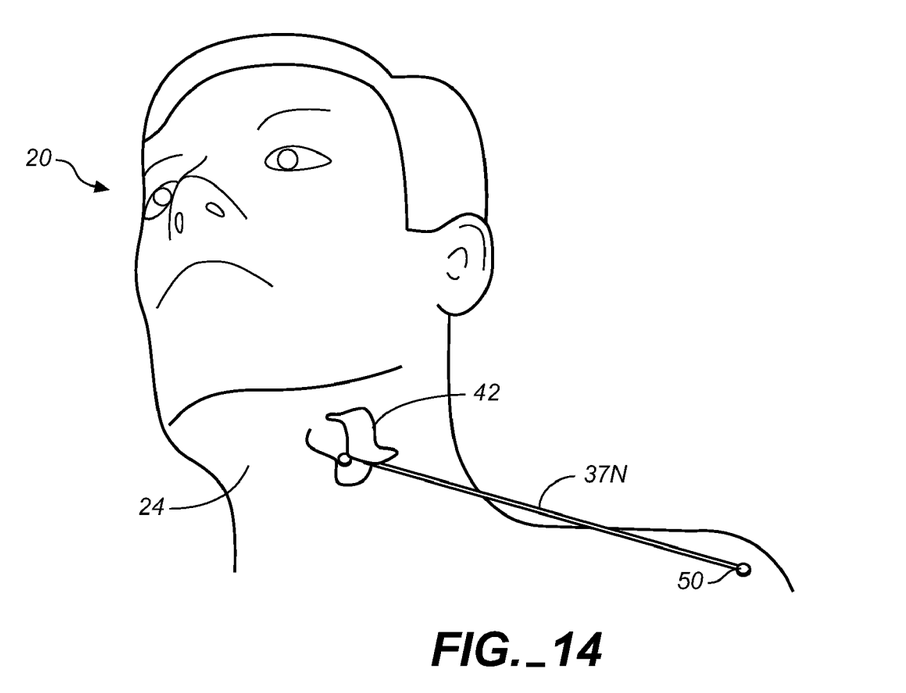
FIG. 14 is a perspective view of a clip type anti-snoring device.

FIG. 14 shows the use of a mechanical clamp 42 to grab a portion of the skin in the throat stimulation area. An elastic connector, 37N attached to anchor point 50 expands a portion of the skin in the throat stimulation area by pulling on the clamp and the skin. The anchor point, 50, is shown on the shoulder, but this anchor point could be on other parts of the body such as the chest, back, or waist. The exact method of attaching to the anchor point is not important.

It should also be noted that clamps similar to 42 in FIG. 14 could be substituted for the adhesive patches 30J and 30JJ in FIGS. 2 and 3. The bow connector 37J would replace the elastic connector in tension 37H in FIG. 14. Tests have been conducted using a spring-loaded miniature clasp normally used to hold women's hair. The holding jaws were covered with foam rubber to improve comfort and reduce slippage. This did work, but it was judged to be less desirable that the preferred embodiment illustrated in FIGS. 2 to 5.

Figure 15:
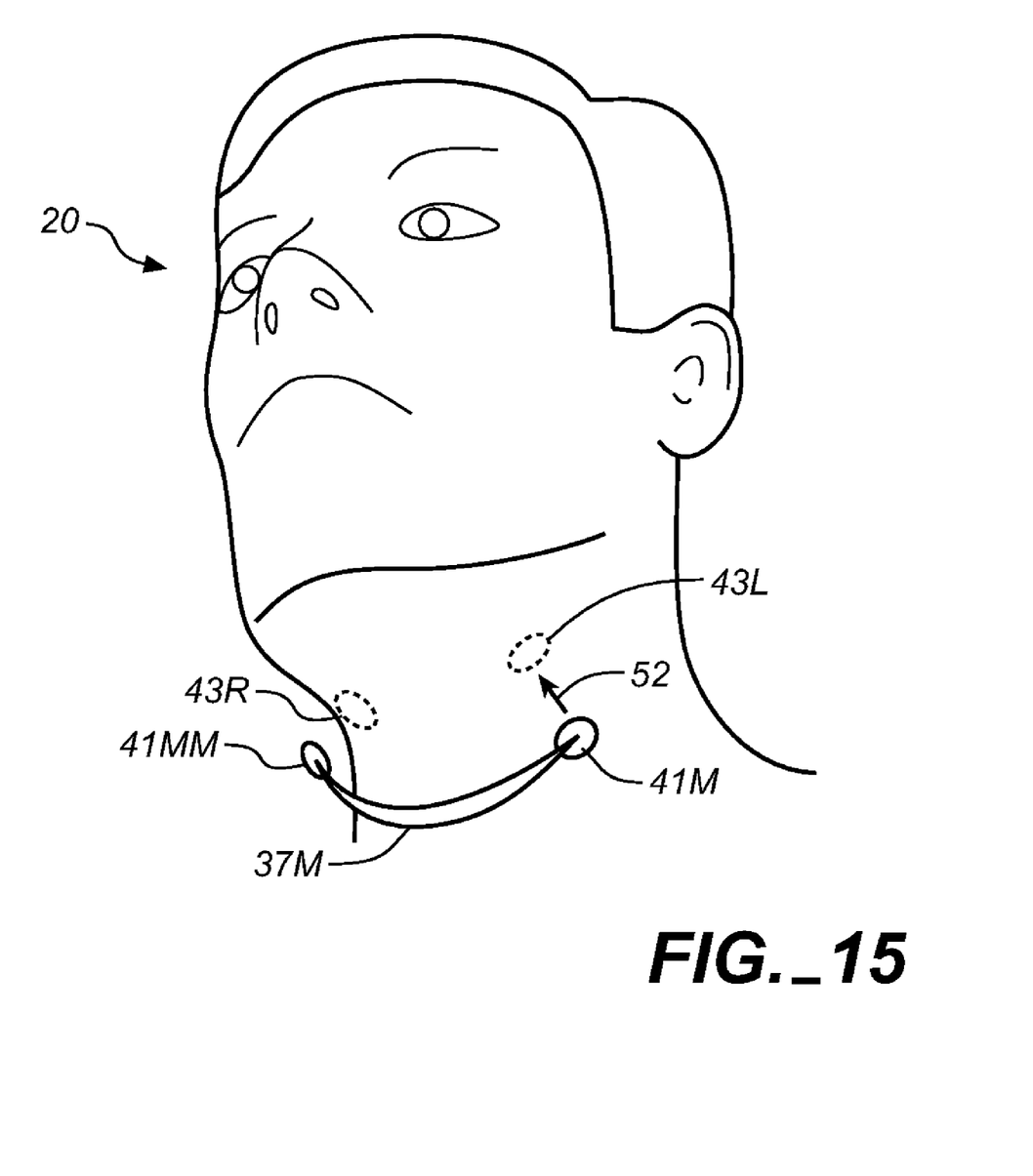
FIG. 15 is a perspective view of magnetic implants and an elastic connector with magnetic means for pulling on the implants.

FIG. 15 shows another mechanical way of causing the throat stimulation area to expand. Implants 43L and 43R (shown in ghost) are magnetic devices buried below the surface of the skin. They are depicted in FIG. 15 as being circular disks, however, they could be other shapes such as rods or even multiple pellets. Preferably they would be ferromagnetic or permanent magnets so that they exhibit a magnetic attraction to an external magnet. For example, 41M and 41MM are permanent magnets attached to the end of bow connector 37M.

FIG. 15 shows the connector 37M and magnets 41M, 41MM slightly removed from the engaged position. Arrow 52 implies the connection. Normally, magnets 41M and 41MM would contact the skin over the magnetic implants 43L and 43R. The operation of this is very similar to the preferred embodiment previously described in FIGS. 2 and 3. The previous explanation for FIGS. 2 and 3 applies to the variation shown in FIG. 15.

The location of throat stimulation area 27F has previously been described as lying along the edge of the trachea. 27F has the property that it can be used either alone or in combination with other responsive points. Using 27F in combination with another responsive point, such as 27E, more fully opens the air passage than either point alone. For example, FIG. 2 shows patches 20J and 30JJ attached to responsive points 27E (left and right). Adding a second set of patches on top of 27F (left and right) and pulling on these areas with a second bow coupler can totally eliminate a snoring sound in a test subject that has sleep apnea. Using just the single device illustrated in FIG. 2 eliminates the apnea episodes, but does not totally eliminate any snoring sound. In people with just a snoring problem (without sleep apnea), the single anti-snoring device illustrated in FIG. 2 is probably sufficient.

The location of throat stimulation area 27F has previously been described. This throat stimulation area is different than the others since it cannot open a blocked air passage by itself. However, 27F has the property that it can more fully open an air passage when used in combination with another throat stimulation area such as 27E. For example, FIG. 2 shows patches 20J and 30JJ attached to responsive points 27E (left and right). Adding a second set of patches on top of 27F (left and right) and pulling on these areas with a second bow coupler can totally eliminate a snoring sound in a test subject that has sleep apnea. Using just the single device illustrated in FIG. 2 eliminates the apnea episodes, but does not totally eliminate any snoring sound. In people with just a snoring problem (without sleep apnea), the single anti-snoring device illustrated in FIG. 2 is probably sufficient.

Responsive point 27G in FIG. 1 lies directly over the center of a man's Adam's apple. This point is not too desirable and it probably requires the additional use of points 27F (left and right). In tests, the best results have experimentally been achieved using responsive points 27E or those points in combination with 27F.

Finally, it should be noted that all the neck patch anti-snoring devices described herein have the following common elements:

There is a means to attach to a part of the throat stimulation area on a human.

There is a bias means for providing a predetermined pulling force to cause at least a portion of the throat stimulation area to expand outward by at least 2.5 mm from its normal position.

The expansion of the throat stimulation area modifies the throat such that the human exhibits improved ease of breathing while sleeping.

The above disclosure is sufficient to enable one of ordinary skill in the art to practice the invention, and provides the best mode of practicing the invention presently contemplated by the inventor. While there is provided herein a full and complete disclosure of the preferred embodiments of this invention, it is not desired to limit the invention to the exact construction, dimensional relationships, and operation shown and described. Various modifications, alternative constructions, changes and equivalents will readily occur to those skilled in the art and may be employed, as suitable, without departing from the true spirit and scope of the invention. Such changes might involve alternative materials, components, structural arrangements, sizes, shapes, forms, functions, operational features or the like.

Therefore, the above description and illustrations should not be construed as limiting the scope of the invention, which is defined by the appended claims.

What is claimed as invention is:

1. An apparatus for treatment of restricted breathing in a human, said apparatus comprising:

at least one arched, resilient and flexible bridge-type support member having a first end and a second end, a length dimension greater than a width dimension, an inside surface, a first pressure surface proximate said first end, and a second pressure surface proximate said second end; and an adhesive skin connecting member disposed on said inside surface between said first and second ends, said skin connecting member for attaching at least a part of said support member to at least a predetermined part of the skin of a throat stimulation area of a user;

wherein, when said first and second pressure surfaces are brought into engagement proximate a user's throat stimulation area and said support member is urged downwardly so as to generally flatten the arched support member and bring said skin connecting member into contact with the throat stimulation area, such engagement gives rise to counteracting forces, wherein said first and second pressure surfaces exert a pushing force on the user's skin and said skin connecting member exerts a pulling force on the user's throat stimulation area, thereby causing at least a portion of the user's skin in the throat stimulation area to expand outwardly from its normal position, wherein the expansion of the skin reshapes the throat such that the user's breathing is substantially improved.

2. The apparatus for treatment of restricted breathing in a human of claim 1, wherein said support member comprises an elongate flexible arch.

3. The apparatus for treatment of restricted breathing in a human of claim 2, wherein said skin connecting member comprises an adhesive disposed on said inside surface of said arch.

4. The apparatus for treatment of restricted breathing in a human of claim 3, wherein said adhesive is a double-sided adhesive tape.

5. A bridge-type anti-snoring device comprising a support member having an inside surface, at least two pressure portions, and at least one skin attachment element disposed on said inside surface, wherein when said at least two pressure portions are placed on a user's neck proximate a responsive point and said skin attachment element is attached to the user's skin proximate the responsive point, said support member exerts a pulling force on said skin attachment element such that the pulling force expands a predetermined area of the user's skin and causes a reduction in snoring;

wherein said skin attachment element is a mechanical clamp for grabbing the skin proximate the user's responsive point.

6. The apparatus of claim 5, wherein said support member is elongate with first and second ends and includes a flexible central portion and first and second support surfaces, one each disposed at said first and second end.

7. The apparatus of claim 6, wherein said central portion is arched and in use is slightly flattened to bring said at least one attachment element into contact with a user's skin.

* * * * *